(12) United States Patent
Williams et al.

(10) Patent No.: US 11,801,054 B2
(45) Date of Patent: Oct. 31, 2023

(54) SURGICAL STAPLER WITH OVAL TOOL ASSEMBLY

(71) Applicant: Covidien LP, Mansfield, MA (US)

(72) Inventors: Justin Williams, Southbury, CT (US); Russell Pribanic, Roxbury, CT (US); David A. Nicholas, Trumbull, CT (US); Andrew M. Miesse, Westbrook, CT (US); Johana M. Marinelli, Avon, CT (US); Stephen S. Chiang, North Haven, CT (US); Drew R. Seils, Guilford, CT (US)

(73) Assignee: Covidien LP, Mansfield, MA (US)

( * ) Notice: Subject to any disclaimer, the term of this patent is extended or adjusted under 35 U.S.C. 154(b) by 151 days.

(21) Appl. No.: 17/392,776

(22) Filed: Aug. 3, 2021

(65) Prior Publication Data

US 2022/0087679 A1    Mar. 24, 2022

Related U.S. Application Data

(60) Provisional application No. 63/081,485, filed on Sep. 22, 2020.

(51) Int. Cl.
*A61B 17/115*    (2006.01)
*A61B 17/3205*   (2006.01)

(52) U.S. Cl.
CPC .... *A61B 17/1155* (2013.01); *A61B 17/32053* (2013.01)

(58) Field of Classification Search
CPC .......................... A61B 17/1114; A61B 17/115
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,047,654 A | 9/1977 | Alvarado |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | | |
|---|---|---|---|
| CA | 908529 A | 8/1972 | |
| CA | 2575657 A1 * | 8/2007 | ........... A61B 17/068 |

(Continued)

OTHER PUBLICATIONS

European Search Report dated Feb. 9, 2022, issued in corresponding EP Appln. No. 21198243, 28 pages.

*Primary Examiner* — Nathaniel C Chukwurah
(74) *Attorney, Agent, or Firm* — Carter, DeLuca & Farrell LLP

(57) ABSTRACT

A surgical stapling device includes a tool assembly for performing anastomoses procedures. The tool assembly includes a reload assembly and an anvil assembly that have oval configurations to facilitate passage of the tool assembly into a body cavity of a patient with minimal trauma.

20 Claims, 10 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |

(56) References Cited

U.S. PATENT DOCUMENTS

| | | |
|---|---|---|
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |

(56) References Cited

U.S. PATENT DOCUMENTS

| | | |
|---|---|---|
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 * | 12/2012 | Viola .................. A61B 17/115 227/181.1 |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,540,132 B2 | 9/2013 | Marczyk et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |

(56) References Cited

U.S. PATENT DOCUMENTS

| | | |
|---|---|---|
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0065398 A1 | 3/2005 | Adams |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0175963 A1 | 8/2007 | Bilotti et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2014/0367444 A1* | 12/2014 | Williams ......... A61B 17/1155 227/175.1 |
| 2015/0083772 A1 | 3/2015 | Miller et al. |

(56) References Cited

U.S. PATENT DOCUMENTS

| | | |
|---|---|---|
| 2015/0173763 A1 | 6/2015 | Liu |
| 2015/0209045 A1 | 7/2015 | Hodgkinson et al. |

FOREIGN PATENT DOCUMENTS

| | | | |
|---|---|---|---|
| CA | 2805365 A1 | 8/2013 | |
| CN | 104039244 A | 9/2014 | |
| CN | 104042288 A | 9/2014 | |
| CN | 104367360 A | 2/2015 | |
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 1671597 A1 | 6/2006 | |
| EP | 2138118 A2 | 12/2009 | |
| EP | 2168510 A1 | 3/2010 | |
| EP | 2238926 A2 | 10/2010 | |
| EP | 2524656 A2 | 11/2012 | |
| EP | 3023077 A1 | 5/2016 | |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2070499 A | 9/1981 | |
| JP | 2004147969 A | 5/2004 | |
| JP | 2013138860 A | 7/2013 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 98/35614 A1 | 8/1998 | |
| WO | 0154594 A1 | 8/2001 | |
| WO | WO-0154594 A1 * | 8/2001 | ......... A61B 17/1114 |
| WO | 02080781 A2 | 10/2002 | |
| WO | 2004047654 A2 | 6/2004 | |
| WO | 2008107918 A1 | 9/2008 | |
| WO | 2013123666 A1 | 8/2013 | |
| WO | 2019091343 A1 | 5/2019 | |
| WO | 2019130087 A1 | 7/2019 | |

\* cited by examiner

US 11,801,054 B2

SURGICAL STAPLER WITH OVAL TOOL ASSEMBLY

CROSS-REFERENCE TO RELATED APPLICATION

This application claims the benefit of and priority to U.S. Provisional Patent Application No. 63/081,485, filed Sep. 22, 2020, the entire contents of which is incorporated by reference herein.

FIELD

This disclosure is generally related to surgical stapling devices and, more particularly, to surgical stapling devices for endoscopic use.

BACKGROUND

Circular stapling devices typically include a tool assembly that has an anvil assembly and a shell or reload assembly. The reload assembly includes a staple cartridge, a staple pusher, and an annular knife. The staple cartridge supports one or more annular rows of staples, and the staple pusher is movable within the staple cartridge to eject the staples from the staple cartridge into the anvil assembly. The annular knife is positioned radially inward of the annular rows of staples and is movable from a retracted position to an advanced position to cut or core tissue against the anvil assembly. Circular stapling devices are commonly used to perform anastomoses procedures including esophagectomy procedures.

During an esophagectomy procedure, all or part of the esophagus is removed and the reload assembly of a circular stapling device is inserted through an intercostal space of a patient into a body cavity. Typically, the anvil assembly is delivered through the esophagus and is attached to the stapling device within or adjacent the body cavity. The stapling device is fired to attach the stomach to the remaining portion of the esophagus. During this procedure, the diameter of the circular stapling device may prohibit insertion of the circular stapling device through the intercostal space. Insertion may require breaking a rib or ribs.

SUMMARY

This disclosure generally relates to a surgical stapling device for performing anastomoses procedures within a body of a patient. The surgical stapling device includes a tool assembly that is configured to access a body cavity with minimal trauma to the patient.

Aspects of the disclosure are directed to a surgical stapling device including an elongate body, an anvil retainer, a reload assembly, and an anvil assembly. The elongate body has a distal portion and a proximal portion. The anvil retainer is supported within and extends from the distal portion of the elongate body and is movable between an advanced position and a retracted position. The reload assembly is supported on the distal portion of the elongate body and includes a shell housing, a staple cartridge supported on the shell housing, staples supported within the staple cartridge, and a staple pushing member that is movable within the housing from a retracted position to an advanced position to eject the staples from the staple cartridge. The staple cartridge has an oval configuration with a width "W" and a length "L". The length "L" is greater than the width "W". The anvil assembly is supported on the anvil retainer and includes an anvil having an oval configuration that corresponds to the oval configuration of the staple cartridge. The anvil assembly is movable in relation to the staple cartridge in response to movement of the anvil retainer between its retracted and advanced positions between open and clamped positions. The anvil is in juxtaposed alignment with the staple cartridge in the clamped position.

In aspects of the disclosure, the anvil assembly includes the anvil, a center rod and an anvil head assembly that is coupled to the center rod by a pivot member and movable in relation to the center rod between a tilted position and an operative position.

In some aspects of the disclosure, the longitudinal axis of the anvil head assembly is aligned with the longitudinal axis of the center rod when the anvil head assembly is in the tilted position.

In certain aspects of the disclosure, the anvil head assembly is urged towards the tilted position.

In aspects of the disclosure, the reload assembly includes a knife carrier and a knife that is supported on the knife carrier.

In some aspects of the disclosure, the knife has an oval configuration and is movable within the shell housing between retracted and advanced positions into engagement with the anvil head assembly.

In certain aspects of the disclosure, the anvil head assembly includes a housing having a post, a backup member, and a cut ring that is supported on the backup member.

In aspects of the disclosure, the post and the anvil define an annular recess, and the backup member and the cut ring are movable within the annular recess from a retracted position to an advanced position.

In some aspects of the disclosure, the backup member includes at least one finger that is engaged with the center rod when the backup member and the cut ring are in their retracted position, and engagement between the at least one finger of the backup member and the center rod retains the anvil head assembly in the operative position.

In certain aspects of the disclosure, the reload assembly includes a coupling mechanism that releasably couples the reload assembly to the distal portion of the elongate body.

In aspects of the disclosure, the surgical stapling device includes a handle assembly that is coupled to the proximal portion of the elongate body.

In aspects of the disclosure, the width "W" is about half of the length "L".

Other aspects of the disclosure are directed to a reload assembly including a shell housing, a staple cartridge, staples, and a staple pushing member. The staple cartridge is supported on the shell housing, and the staples are supported within the staple cartridge. The staple pushing member is movable within the shell housing from a retracted position to an advanced position to eject the staples from the staple cartridge. The staple cartridge has an oval configuration with a width "W" and a length "L" that is greater than the width "W".

Other aspects of the disclosure are directed to an anvil assembly including a center rod and an anvil head assembly. The anvil head assembly is supported on the center rod by a pivot member and is pivotable in relation to the center rod from an operative position to a tilted position. The anvil head assembly includes a housing having a post, an anvil supported on the housing, a backup member, and a cut ring that is supported on the backup member. The post and the anvil define an annular recess. The backup member and the cut ring are movable within the annular recess from a retracted position to an advanced position. The anvil has an oval configuration having a width "W" and a length "L" that is greater than the width "W".

Other aspects, features, and advantages will be apparent from the description, the drawings, and the claims that follow.

BRIEF DESCRIPTION OF DRAWINGS

Various aspects and features of the disclosure are described with reference to the drawings wherein like numerals designate identical or corresponding elements in each of the several views and.

DETAILED DESCRIPTION

Figure 1:
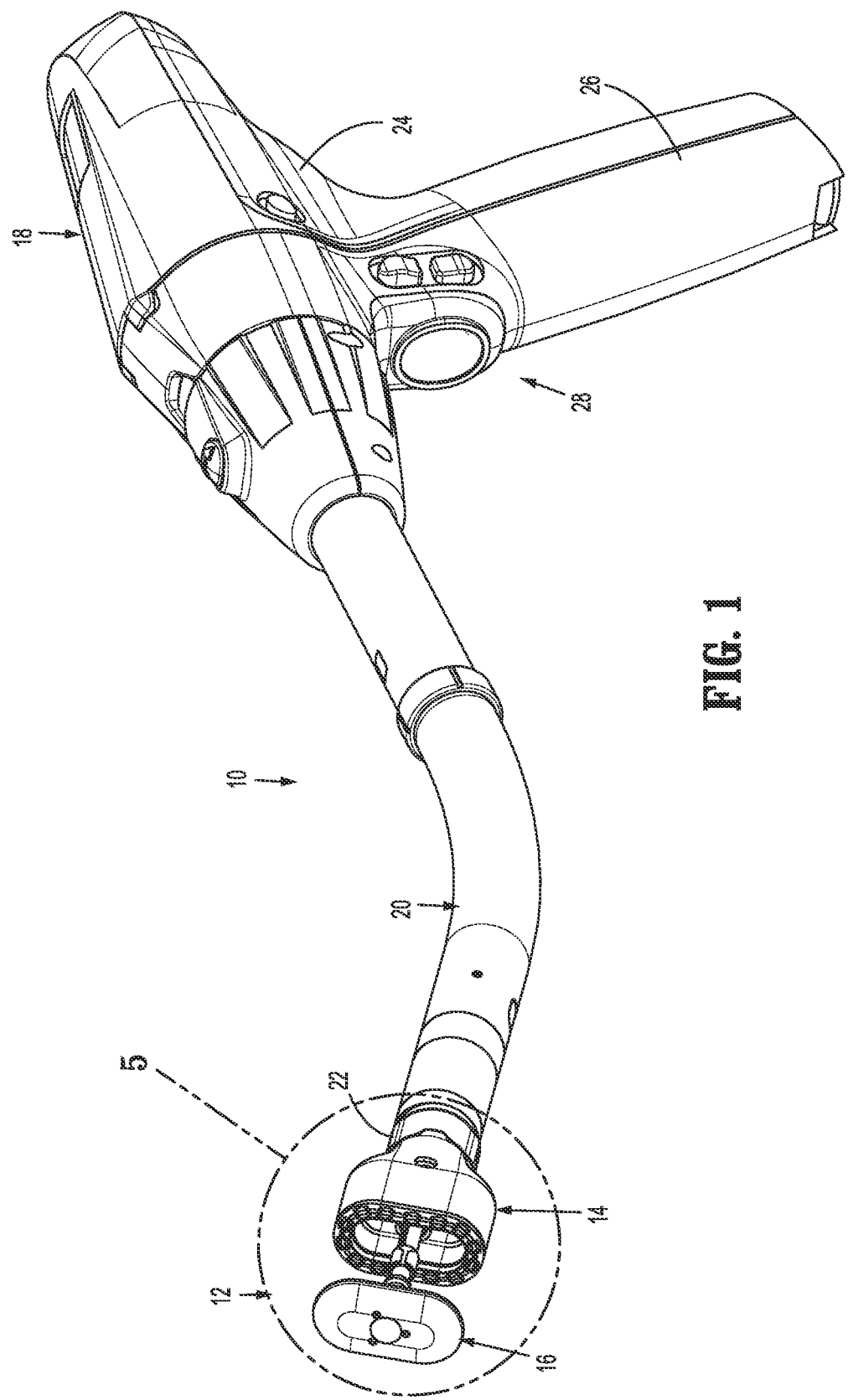
FIG. 1 is a side perspective view of a surgical stapling device according to aspects of the disclosure.

The disclosed surgical stapling device including a tool assembly according to various aspects of the disclosure will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. The term "endoscopic" is used generally used to refer to endoscopic, laparoscopic, arthroscopic, and/or any other procedure conducted through small diameter incision or cannula. In addition, the term "about" is intended to include a range that includes listed parameter and plus or minus ten percent of the listed parameter. Further, the term "clinician" is used generally to refer to medical personnel including doctors, nurses, and support personnel.

This disclosure is directed to a surgical stapling device for performing anastomoses procedures. The surgical stapling device includes a tool assembly that has a reload assembly and an anvil assembly that have oval configurations to facilitate passage of the tool assembly into a body cavity of a patient while minimizing trauma to the patient.

FIG. 1 illustrates a stapling device 10 having a tool assembly 12 including a reload assembly 14 and an anvil assembly 16 in accordance with aspects of the disclosure. The stapling device 10 includes a handle or actuator assembly 18, an elongate body or adaptor assembly 20, the reload assembly 14, and the anvil assembly 16. The anvil assembly 16 is supported for movement in relation to the reload assembly 14 between an open or unclamped position (FIG. 1) and a clamped position (not shown). In aspects of the disclosure, the reload assembly 14 includes a proximal portion 22 that is releasably coupled to a distal portion of the adaptor assembly 14 and the adaptor assembly 20 includes a proximal portion that is releasably coupled to the handle assembly 18. Alternately, it is envisioned that the reload assembly 14 can be fixedly secured to the adaptor assembly 20 and/or the adaptor assembly 20 can be fixedly secured to the handle assembly 18.

The handle assembly 18 includes a body 24 that defines a stationary hand grip 26 that supports actuation buttons 28 for controlling operation of various functions of the stapling device 10 including approximation of the reload assembly 14 and anvil assembly 16, firing of staples from the reload assembly 14, and cutting or coring of tissue.

The stapling device 10 is illustrated as an electrically powered stapling device and includes the handle assembly 18 that is electrically powered and may support one or more batteries (not shown). The adaptor assembly 20 translates power from the handle assembly 18 to the reload and anvil assemblies 14 and 16, respectively, to move the tool assembly 12 between the open and clamped positions and to staple and cut tissue. Examples of electrically powered stapling devices can be found in U.S. Pat. Nos. 9,055,943, 9,023,014, and U.S. Publication Nos. 2018/0125495, and 2017/0340351. Alternately, it is envisioned the tool assembly 12 could be incorporated into a manually powered stapling device such as disclosed in, e.g., U.S. Pat. No. 7,303,106 (the '106 patent), or a stapling device that is configured for use with a robotic system as disclosed in, e.g., U.S. Pat. No. 9,962,159, that does not include a handle assembly.

Figure 2:
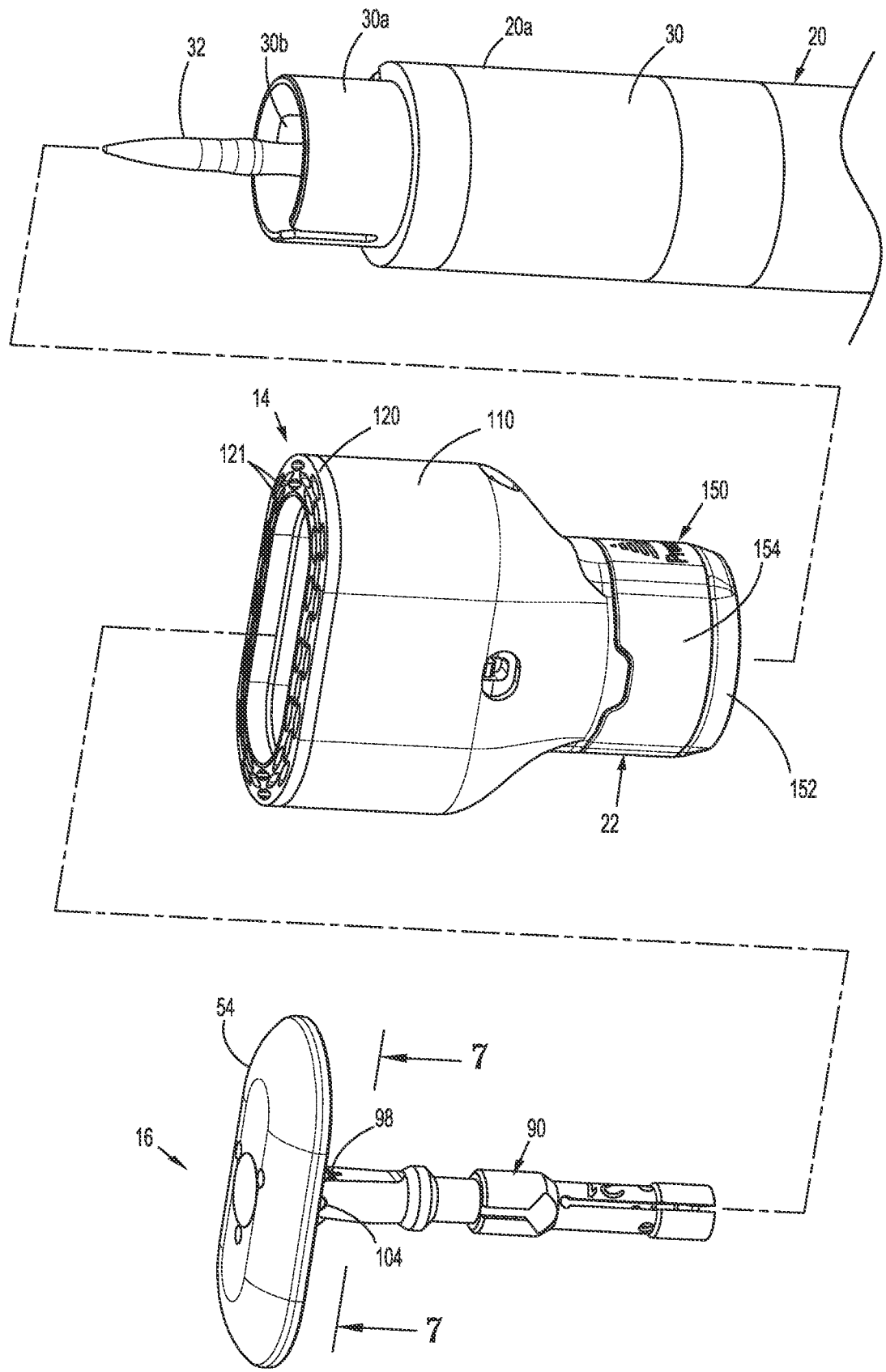
FIG. 2 is a side perspective view of a distal portion of the surgical stapling device shown in FIG. 1 with an anvil assembly, reload assembly, and body portion separated from each other.

FIG. 2 illustrates a distal portion of the stapling device 10 including a distal portion 20a of the adaptor assembly 20, the reload assembly 14, and the anvil assembly 16. The adaptor assembly 20 includes an outer tube 30 and an anvil retainer 32 that is movable within the outer tube 30 between retracted and advanced positions. The anvil assembly 16 is releasably coupled to the anvil retainer 32 and is movable with the anvil retainer 32 between the advanced and retracted positions to move the tool assembly 12 between the open and clamped positions. The outer tube 30 includes a distal portion 30a that defines a window 30b and supports the reload assembly 14.

Figure 3:
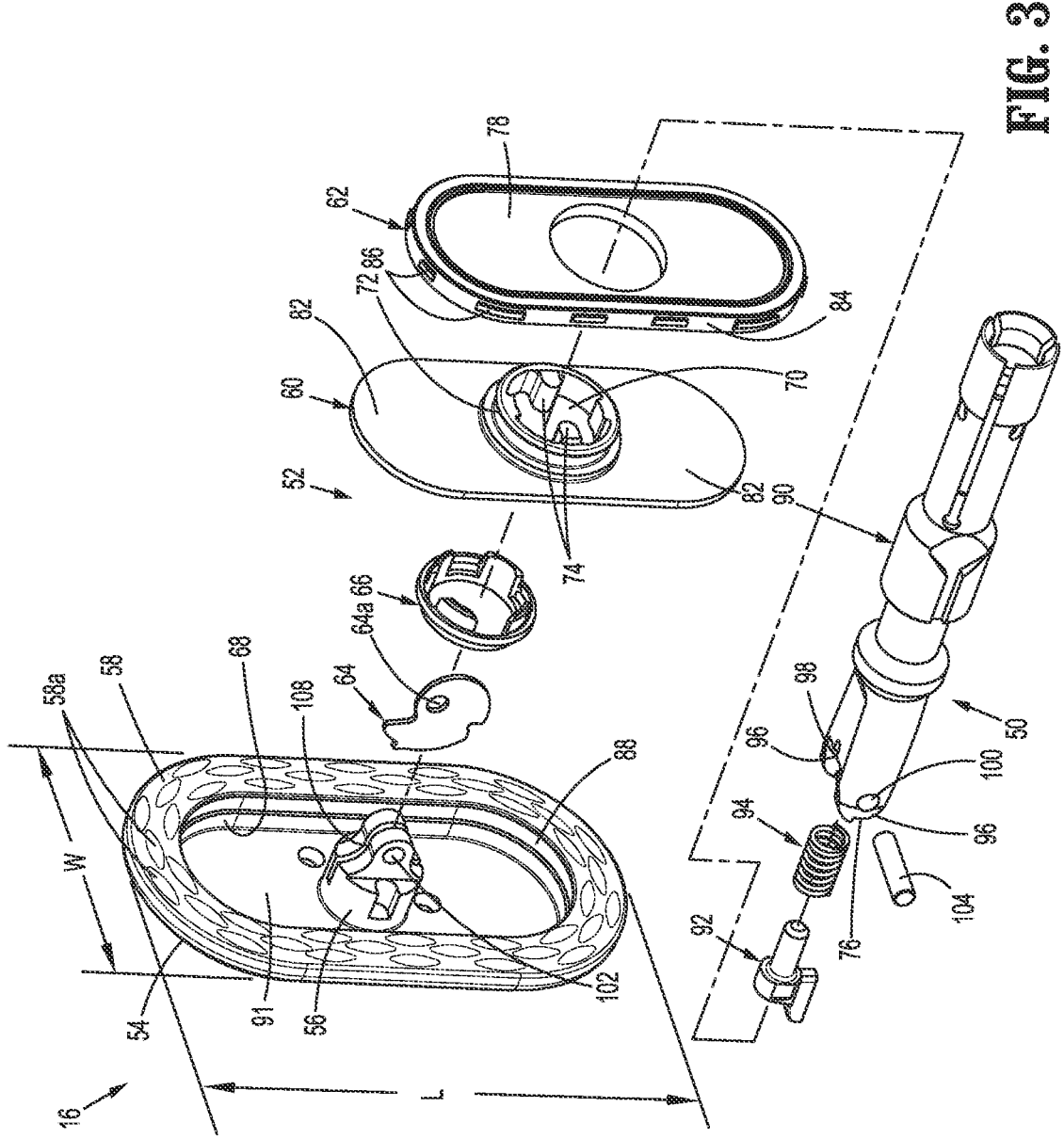
FIG. 3 is an exploded view of the anvil assembly shown in FIG. 2.

FIG. 3 illustrates the anvil assembly 16 which includes a center rod assembly 50 and an anvil head assembly 52 that is pivotally supported on a distal portion of the center rod assembly 50. The anvil head assembly 52 includes a housing 54 that includes a post 56, an anvil 58, a backup member 60, a cut ring 62, a cam latch member 64, and a deformable support member 66. In aspects of the disclosure, the housing 54 including the post 56, and the anvil 58 are monolithically formed. Alternately, any one or all of the housing 54, post 56, and anvil 58 can be formed separately and secured together using any known fastening technique including welding, crimping or the like. The housing 54 of the anvil head assembly 52 defines a recess 68 that is positioned between the post 56 and the anvil 58 with the post 56 centrally located within the recess 68. The anvil 58 defines a plurality of staple deforming pockets 58a for receiving and deforming staples ejected from the reload assembly 14. In aspects of the disclosure, the anvil 58, the backup member 60, and the cut ring 62 have oval configurations with length dimensions "L" defined by curved end walls that greater than width dimensions "W" defined by linear side walls. The backup member 60 and the cut ring 62 are received within the recess 68 of the housing 54 which also has an oval configuration that corresponds to the configuration of the backup member 60 and cut ring 62.

The backup member 60 defines a central opening 70 that receives the post 56 of the housing 54 of the anvil head assembly 52 to facilitate movement of the backup member 60 about the post 56 from a pre-fired, retracted position (FIG. 10) to a post-fired, advanced position (not shown) within the recess 68 of the housing 54. The backup member 60 includes a raised flange 72 that is positioned about the opening 70. Although the raised flange 72 is illustrated as having a circular shape, other configurations are envisioned, e.g., square, rectangular, triangular, etc.

The backup member 60 includes a pair of inwardly extending fingers 74 that are movable into and out of engagement with a distal flat 76 of the center rod assembly 50 of the anvil assembly 16. When the fingers 74 are engaged with the distal flats 76, the engagement prevents pivotal movement of the anvil head assembly 52 in relation to the center rod assembly 50. When the backup member 60 moves out of engagement with the distal flats 76, the anvil head assembly 52 can pivot in relation to the center rod assembly 50 between an operative position (FIG. 2) and a tilted position (FIG. 11) as described in further detail below. In aspects of the disclosure, the backup member 60 is formed from a hard material such as metal although other materials of construction are envisioned. U.S. Pat. No. 8,540,132 (the '132 patent) discloses the construction and operation of a tilt anvil assembly that includes a backup member and cut ring assembly that are movably positioned about a post of an anvil head of an anvil assembly. Although not described in detail herein, the anvil head assembly 52 can be pivotable between a tilted pre-fired position, an operative position (FIG. 10), and a post-fired tilted position. The pre-fired tilted position and the post fired tilted position allow the anvil assembly 16 to be delivered to and removed from a body cavity through a body lumen, e.g., the esophagus, with minimal trauma to the body lumen. See U.S. Pat. No. 8,328,063 for a detailed description of a tiltable anvil assembly such as described.

In aspects of the disclosure, the cut ring 62 (FIG. 4) includes an oval body 78 that defines a central opening 80 that receives the raised flange 72 of the backup member 60 and the cut ring 62 is secured to a proximal surface 82 of the backup member 60 about the raised flange 72. In certain aspects of the disclosure, the cut ring 62 is press-fit onto the raised flange 72 of the backup member 60 to secure the body 78 of the cut ring 62 onto the backup member 76.

Figure 10:
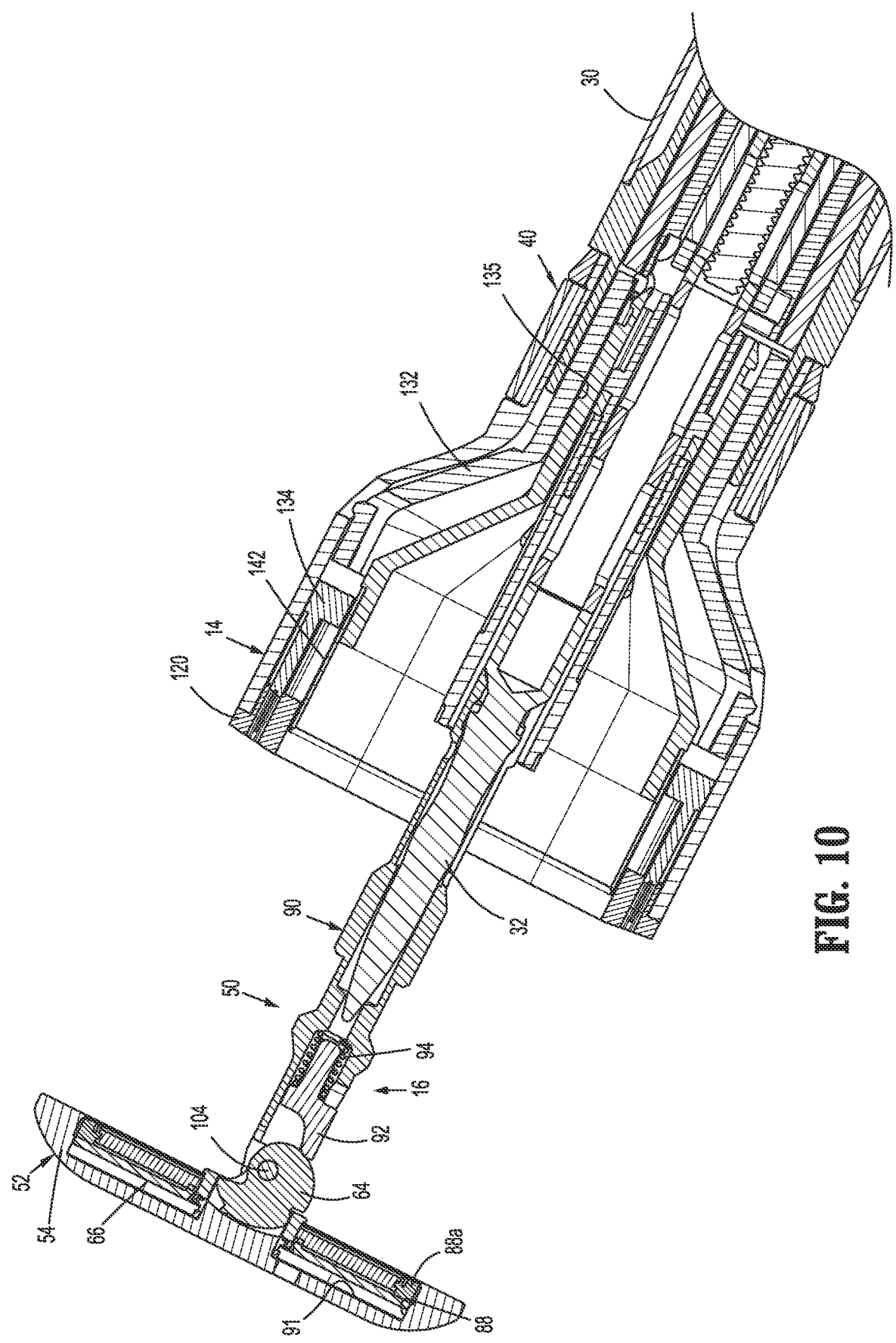
FIG. 10 is a cross-sectional view taken along section line 10-10 of FIG. 5.

The body 78 of the cut ring 62 includes an outer wall 84 that has a series of projections 86 and the housing 54 of the anvil assembly 16 includes an inner wall 88 that defines an annular groove 88a (FIG. 10). In aspects of the disclosure, the projections 86 of the cut ring 62 are slidably received within the annular groove 88a to guide movement of the cut-ring 62 and backup member 62 between their advanced and retracted positions within the recess 68 of the housing 54 of the anvil assembly 16.

The deformable support member 66 is supported about the post 56 of the housing 54 of the anvil head assembly 52 between a proximal surface of the backup member 60 and an inner surface 91 of the housing 54. The deformable support member 66 retains the backup member 60 and the cut ring 62 in their retracted positions within the recess 68 of the housing 54 until a pre-determined force sufficient to deform the support member 66 is applied to the cut ring 62 during firing of the stapling device 10 (FIG. 1) by a knife 142 of the reload assembly 14. When the support member 66 is deformed, the backup member 60 and the cut ring 62 move within the recess 68 about the post 56 to their advanced positions.

The center rod assembly 50 includes a center rod 90, a plunger 92, and a plunger spring 94. The center rod 90 has a first end that includes spaced arms 96 that define a cavity 98 (FIG. 3) that receives a portion of the post 56 of the housing 54 of the anvil head assembly 52. Each of the spaced arms 96 of the center rod 90 defines one of the distally facing flats 76 and defines a transverse through bore 100. The transverse through bores 100 define an axis that intersects a central longitudinal axis of center rod 90. Alternately, the axis defined by the through bores 100 can be offset from the longitudinal axis of center rod 90.

Figure 11:
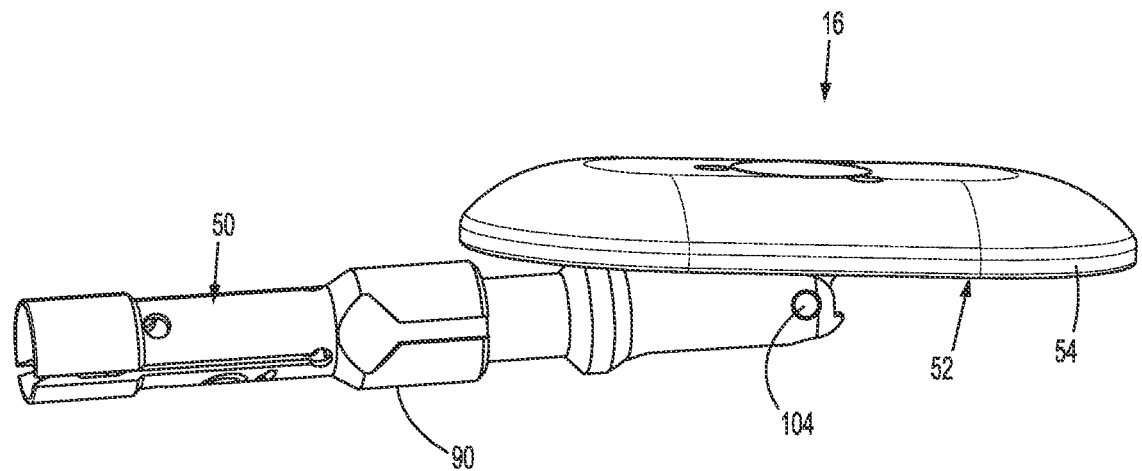
FIG. 11 is a side perspective view of the anvil assembly shown in FIG. 2 in a tilted position.

The post 56 of the housing 54 of the anvil head assembly 52 is positioned within the cavity 98 defined between the spaced arms 96 of the center rod 90 and defines a transverse through bore 102. A pivot member 104 extends through the through bores 100 of the spaced arms 96 and the through bore 100 of the post 56 to pivotally secure the post 56 to the center rod 90 such that the anvil head assembly 52 is pivotally mounted to the center rod assembly 50 between the operative position (FIG. 10) and at least one tilted position (FIG. 11). In the operative position, the longitudinal axes of the center rod 90 and the post 56 are substantially aligned and the anvil 58 faces the reload assembly 14. In the tilted position, the longitudinal axes of the center rod 90 and the post 56 define an acute angle. The distally facing flats 76 formed on the distal end of spaced arms 96 of the center rod 90 abut the inwardly extending fingers 74 of the backup member 60 when the backup member 60 is in its retracted position within the recess 68 of the housing 54 of the anvil head assembly 52 to releasably retain the anvil head assembly 52 in the operative position.

The cam latch member 64 is received in a slot 108 defined within the post 56 of the anvil head assembly 52. The cam latch member 64 defines a through bore 64a (FIG. 3) that receives the pivot member 104 such that the cam latch member 64 is pivotally supported about the pivot member 104 within the slot 108. The plunger 92 is urged by the plunger spring 94 into engagement with the cam latch member 64 and a proximal end of the post 56 of the anvil head assembly 52 to urge the anvil head assembly 52 about the pivot member 104 towards the tilted position (FIG. 11). The cam latch member 64 engages an inner surface of the backup member 60 (FIG. 10) to prevent movement of the backup member 60 and the cut ring assembly 62 from their advanced positions within the recess 68 back to their retracted positions after the stapling device 10 is fired.

For a more detailed description of an anvil assembly including operation of the cam latch member 64, the plunger 92, and the plunger spring 94, see the '132 patent.

Figure 4:
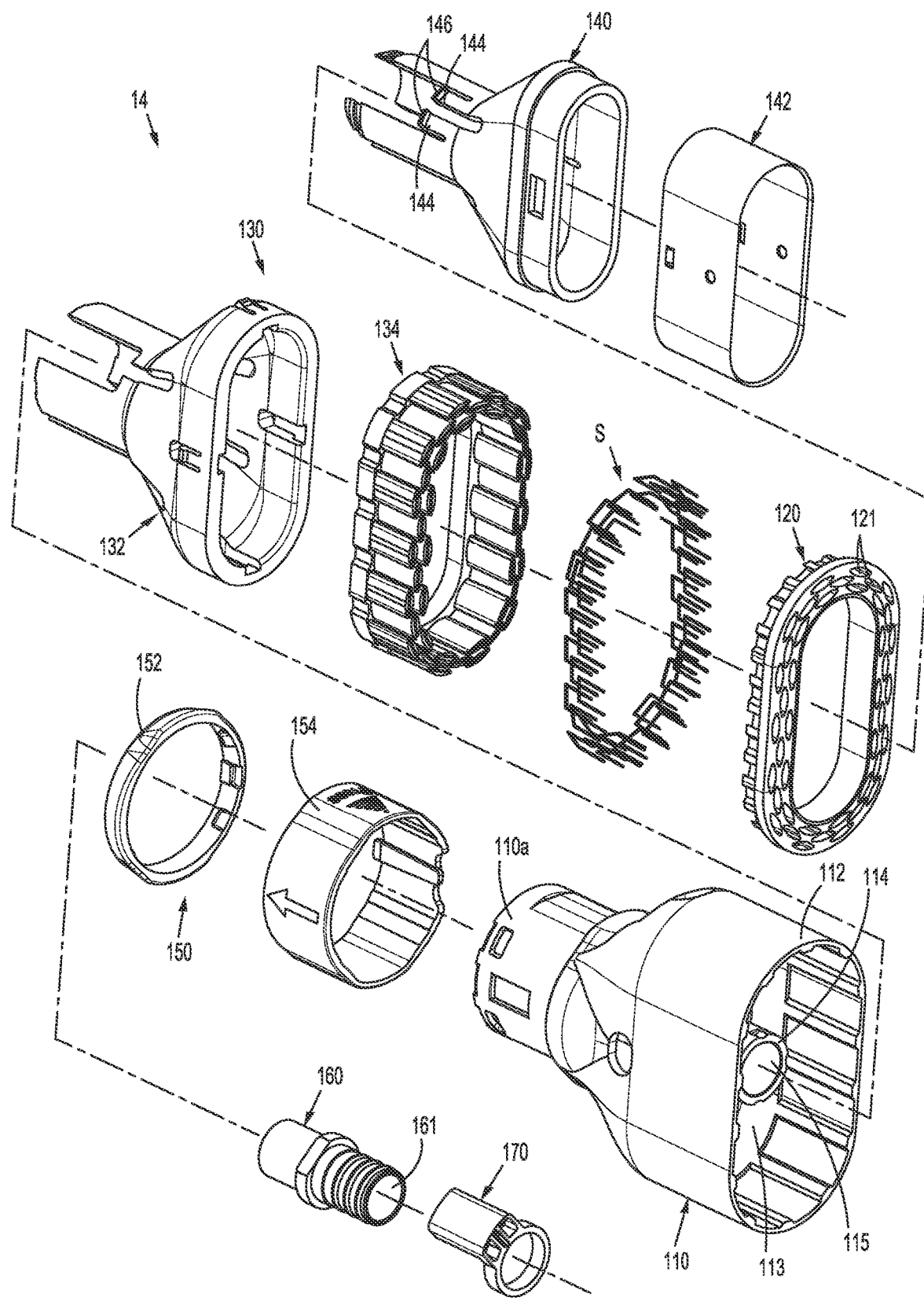
FIG. 4 is an exploded view of the reload assembly shown in FIG. 2.

FIG. 4 illustrates the reload assembly 14 which includes a shell housing 110, a staple cartridge 120, a plurality of staples "S" received within the staple cartridge 120, a staple pusher assembly 130, a knife carrier 140, and an annular knife 142 supported on the knife carrier 140. The staple cartridge 120 is annular and defines annular rows of staple receiving pockets 121. Each of the staple receiving pockets 121 receives one of the plurality of staples "S". In aspects of the disclosure, the annular staple cartridge 120 has an oval configuration that corresponds to the configuration of the anvil 58 (FIG. 3) of the anvil assembly 16 and has a width "W" defined by linear side walls and a length "L" defined by curved end walls that is substantially the same as the anvil 58.

The pusher assembly 130 of the reload assembly 100 includes an annular pusher 132 and a staple pushing member 134 that together define a longitudinal through bore 135. The annular pusher 132 has a distal portion that abuts a proximal portion of the staple pushing member 134 such that distal movement of the annular pusher 132 within the shell housing 110 causes distal movement of the staple pushing member 132 within the shell housing 110. The staple pushing member 134 of the reload assembly 100 has a plurality of fingers 136. Each of the plurality of fingers 136 is received within a respective one of the staple pockets 121 of the staple cartridge 120 and is movable through the respective staple pocket 121 to eject the staples "S" from the staple pockets 121 when the staple pushing member 132 is moved from its retracted position to its advanced position within the shell housing 110.

The shell housing 110 of the reload assembly 100 includes an outer housing portion 112 and an inner housing portion 114 that is spaced from the outer housing portion 112 to define an annular cavity 113 that receives the pusher assembly 130, the knife carrier 140, and the annular knife 142. The annular cavity 113 has an oval configuration. The pusher assembly 130, the knife carrier 140, and the annular knife 142 have oval configurations that correspond to the configuration of the staple cartridge 120 and are movable within the annular cavity 113 between retracted and advanced positions when the stapling device 10 is fired to staple and cut tissue clamped between the anvil assembly 16 and the reload assembly 14. In aspects of the disclosure, the pusher assembly 130 can be movable independently of the knife carrier 140 or in unison with the knife carrier 140 to eject staples "S" from the staple cartridge 120 and cut tissue.

The reload assembly 14 includes a proximal portion that supports a coupling mechanism 150 that is operable to couple the reload assembly 14 to the adaptor assembly 20 (FIG. 1) of the stapling device 10. The coupling mechanism 150 includes a retaining member 152 and a coupling member 154. The coupling member 154 is received about a proximal portion 110a of the shell housing 110 and engages a distal end of the adaptor assembly 20 to couple the reload assembly 100 to the adaptor assembly 14.

The inner housing portion 114 of the shell housing 110 defines a through bore 115 that receives the anvil retainer 32 (FIG. 2) and the center rod 90 of the anvil assembly 16 (FIG. 2) when the anvil assembly 16 is coupled to the anvil retainer 32 and the stapling device 10 is moved to the clamped position. The through bore 115 receives a bushing 160 that defines a through bore 161 that is coaxial with the through bore 115. The bushing 160 is formed of a high strength material, e.g., metal, to provide added strength to the inner housing portion 114 of the shell housing 110. In aspects of the disclosure, the bushing 160 supports an e-prom holder 170 that is clamped between the bushing 160 and the inner housing portion 114 of the shell housing 110. The e-prom holder supports and e-prom chip (not shown) that communicates with the adaptor assembly 20 (FIG. 1) to provide information to the adaptor assembly 20 and the handle assembly 18 related to characteristics of the reload assembly 14.

Figure 5:
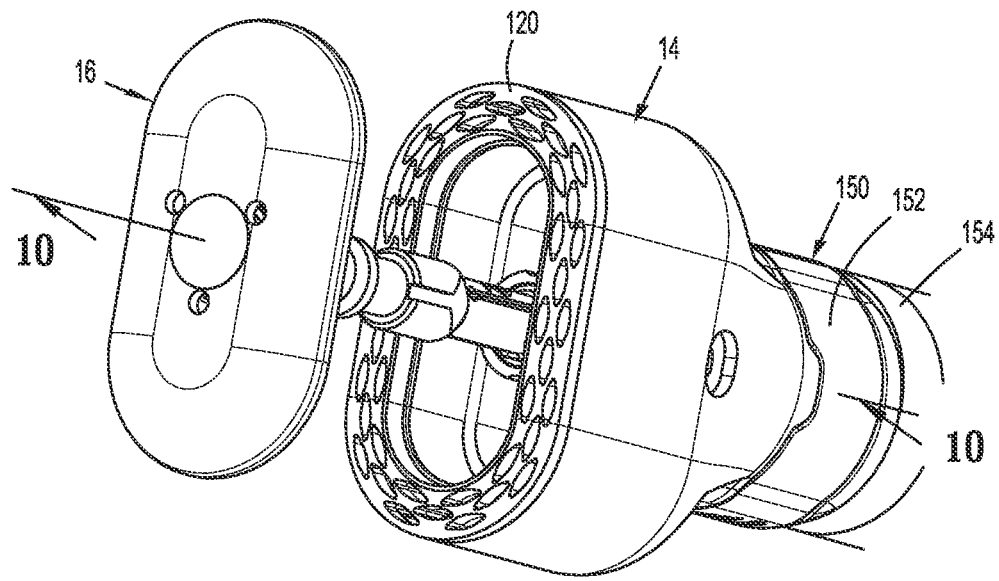
FIG. 5 is an enlarged view of the area of detail shown in FIG. 1.
Figure 6:
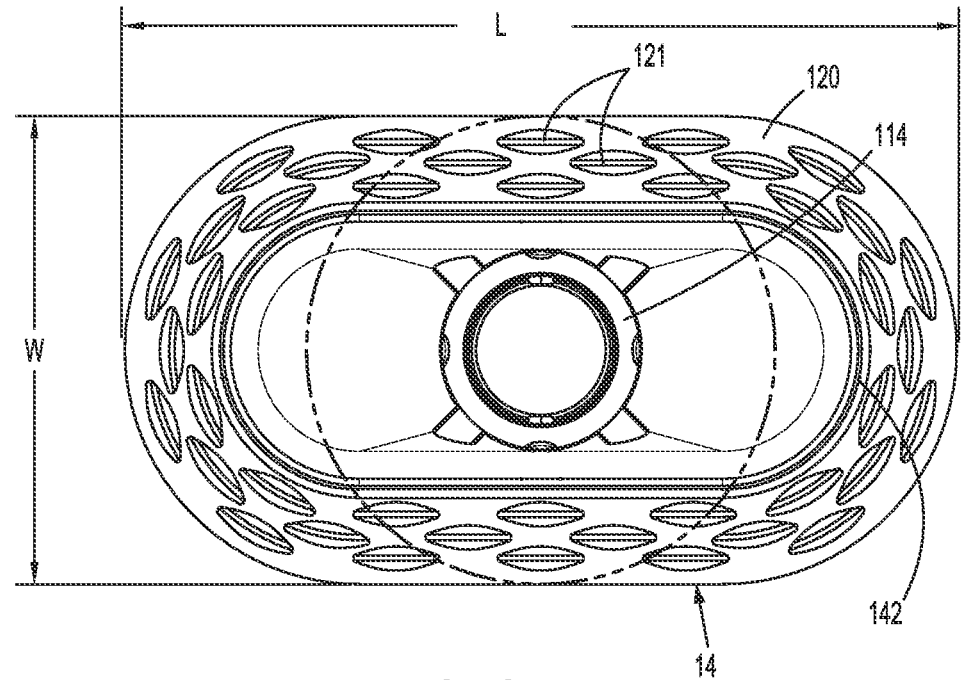
FIG. 6 is view from the distal end of the reload assembly of the surgical stapling device shown in FIG. 2.
Figure 7:
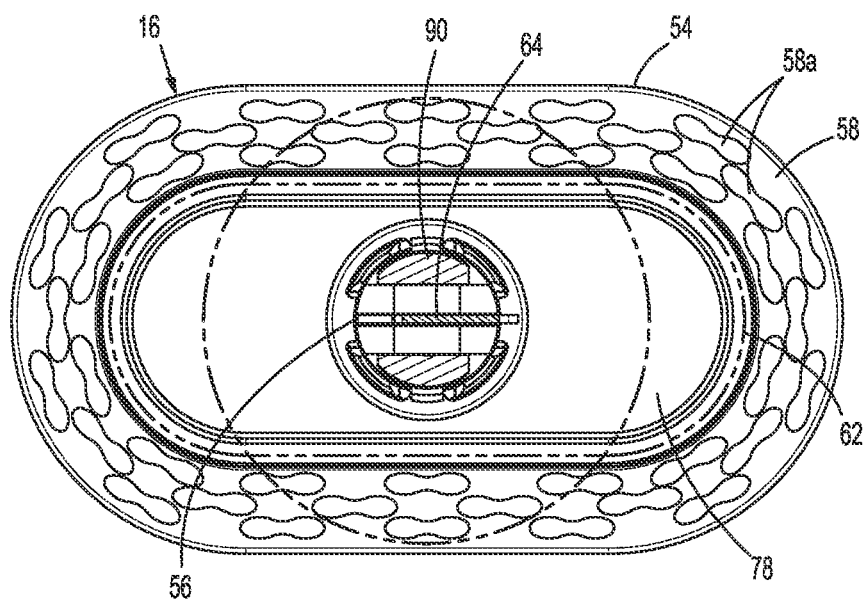
FIG. 7 is a cross-sectional view taken along section line 7-7 of the anvil assembly shown in FIG. 2.

FIGS. 5-7 illustrate the tool assembly 12 including the reload assembly 14 and the anvil assembly 16. As described above, the staple cartridge 120 of the reload assembly 14 has an oval configuration that corresponds to the oval configuration of the anvil 58 (FIG. 7) and includes a width "W" and a length "L". In aspects of the disclosure, the oval configuration of the staple cartridge 120 is long and thin to facilitate insertion through the intercostal space of a patient to perform an anastomosis procedure such as during an esophagectomy procedure. In some aspects of the disclosure, the width "W" is about half of the length "L". In certain aspects of the disclosure, the width "W" is about 21 mm and the length "L" is about 42 mm. It is envisioned that the width "W" and the length "L" of the staple cartridge 120 and the anvil 58 can be selected to have a variety of different dimensions to suit a particular surgical procedure.

Figure 8:
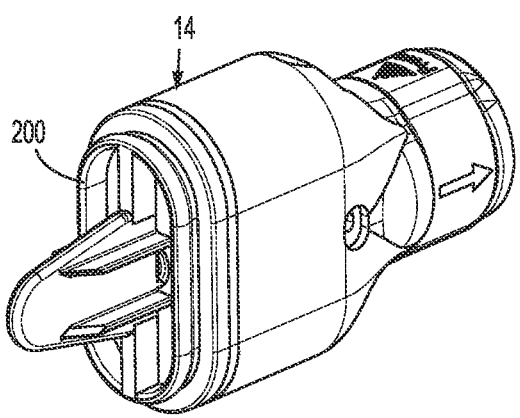
FIG. 8 is a perspective view of the reload assembly shown in FIG. 2 with a trans-anastomotic insertion device secured to the reload assembly.

FIG. 8 illustrates the reload assembly 14 with a trans-anastomotic insertion device 200 secured to a distal end of the reload assembly 14. The trans-anastomotic insertion device 200 (hereinafter "TAID") is used to dilate a port through which the reload assembly 14 is inserted into a body cavity. The TAID can be formed of disposable plastic or reusable metal, e.g., stainless steel, and includes a dilator tip 202. The dilator tip 202 has a distal end and a proximal end and diverges from the distal end towards the proximal end.

Figure 9:
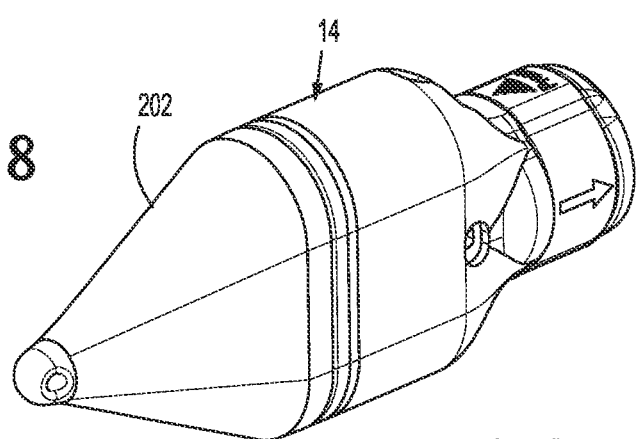
FIG. 9 is a perspective view from the distal end of the reload assembly shown in FIG. 2 with a shipping cap secured to the reload assembly.

FIG. 9 illustrates a shipping cap 202 secured to the distal end of the reload assembly 14. The shipping cap 202 is secured to the reload assembly 14 to retain staples within the staple cartridge 120 and to prevent premature advancement of the staple pushing member 134 (FIG. 4) and knife carrier 140 within the shell housing 110 (FIG. 4) prior to attachment of the reload assembly 14 to the adaptor assembly 20 (FIG. 1).

FIG. 10 illustrates the distal portion of the stapling device 10 with the tool assembly 12 in its unclamped or open position prior to firing of the stapling device 10. As illustrated, the backup member 60 and the cut ring 62 are in their retracted positions (FIG. 10) with the cut ring 62 supported about the flange 72 of the backup member 60. The support member 66 is positioned between the backup member 60 and the inner surface 91 of the housing 54 of the anvil head assembly 52 in an undeformed condition to obstruct movement of the backup member 60 and cut ring assembly 62 from their retracted positions towards their advanced positions within the recess 68 of the housing 54.

With the backup member 60 in its retracted position, the inwardly extending fingers 74 (FIG. 3) of the backup member 60 are supported on the distally facing flats 76 (FIG. 3) of the center rod 90 such that the anvil head assembly 52 is retained in the operative position. As discussed above, the plunger 92 of the center rod assembly 50 is positioned to urge the cam latch member 64 and the anvil head assembly 52 about the pivot member 104 towards the tilted position (FIG. 11). When the stapling device 10 is fired to advance the annular knife 142 into the cut ring 62, the cut ring 62 and the backup member 60 are driven from their retracted positions to their advanced positions and deform the support member 66. When the fingers 74 move to a position spaced from the distal flats 76 of the center rod assembly 50, the biasing member 94 and plunger 92 urge the anvil head assembly 52 about the pivot member 104 towards the tilted position. For a more detailed description of the operation of the anvil assembly, see the '132 patent and U.S. Pat. No. 7,303,106.

Figure 12:
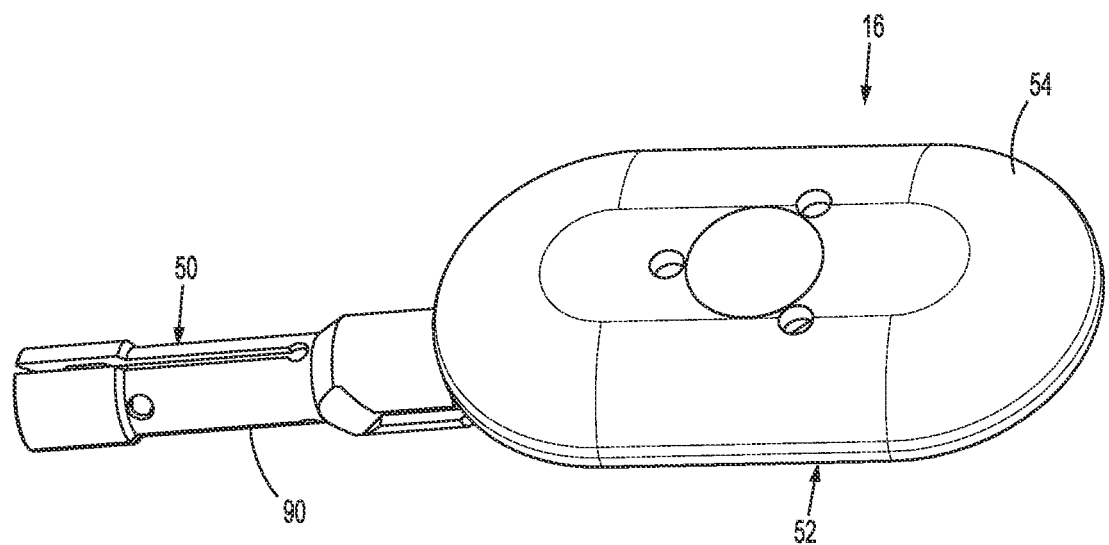
FIG. 12 is a side perspective view of the anvil assembly shown in FIG. 11 rotated ninety degrees.

FIGS. 11 and 12 illustrate the anvil assembly 16 in its tilted position. As illustrated, the anvil head assembly 52 defines a longitudinal axis that is substantially coaxial with a longitudinal axis of the center rod 90 of the center rod 50 of the anvil assembly 16.

Figure 13:
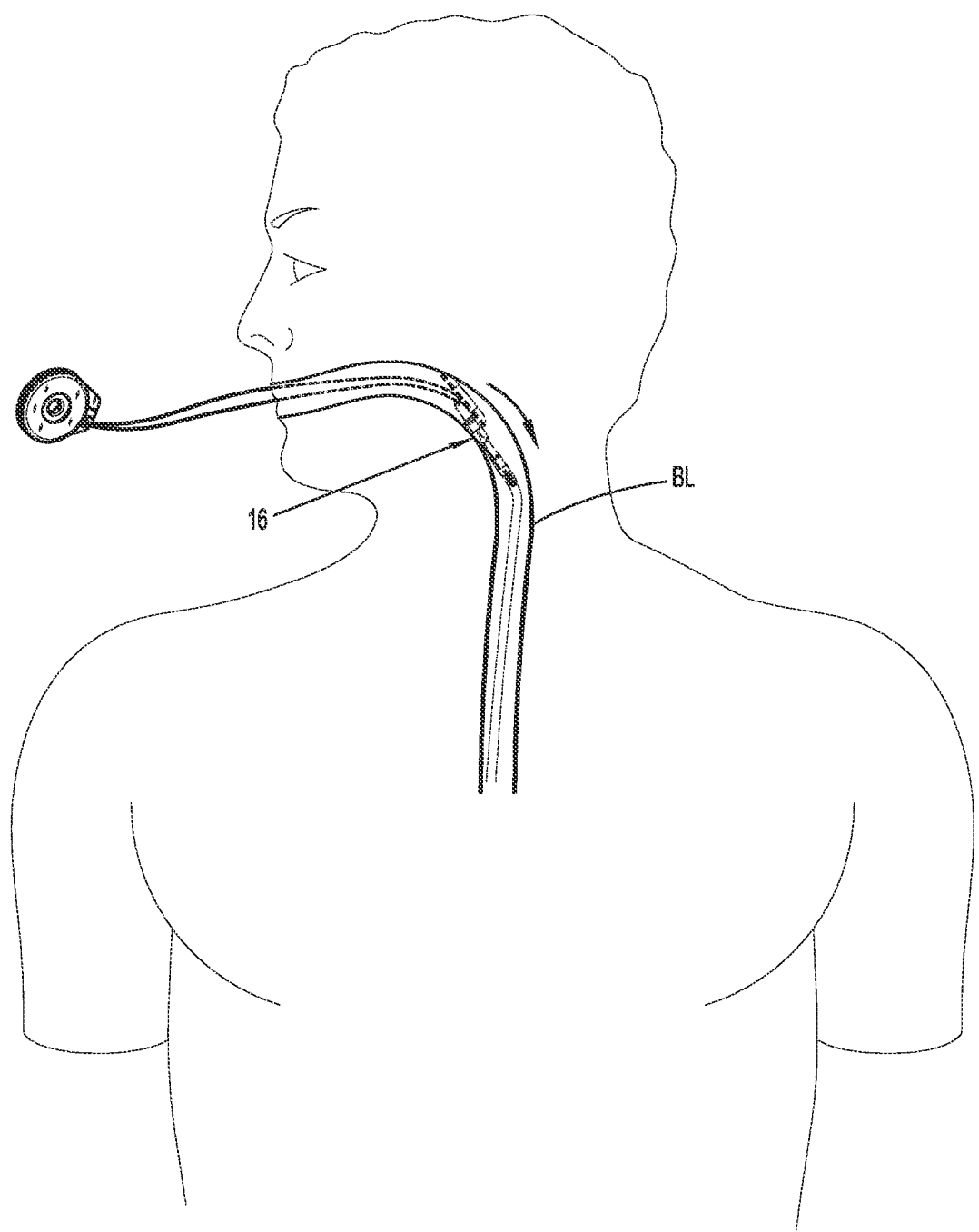
FIG. 13 is a side perspective view of the anvil assembly shown in FIG. 12 as the anvil assembly is guided through the esophagus of a patient.

FIG. 13 illustrates delivery of the anvil assembly 16 to a body cavity "BC" (FIG. 14) through a body lumen "BL", e.g., esophagus, during a surgical procedure, e.g., esophagectomy. The anvil assembly 16 is delivered in its pre-fired tilted position through the body lumen, where it can be coupled to the anvil retainer 32 (FIG. 14) of the stapling device 10. Trauma that may result from delivery of the anvil assembly 16 through a body lumen "BL" to a surgical site is minimized by aligning the longitudinal axes of the anvil head assembly 52 and the center rod 90 and tilting the anvil head assembly 52 to a low profile position.

Figure 14:
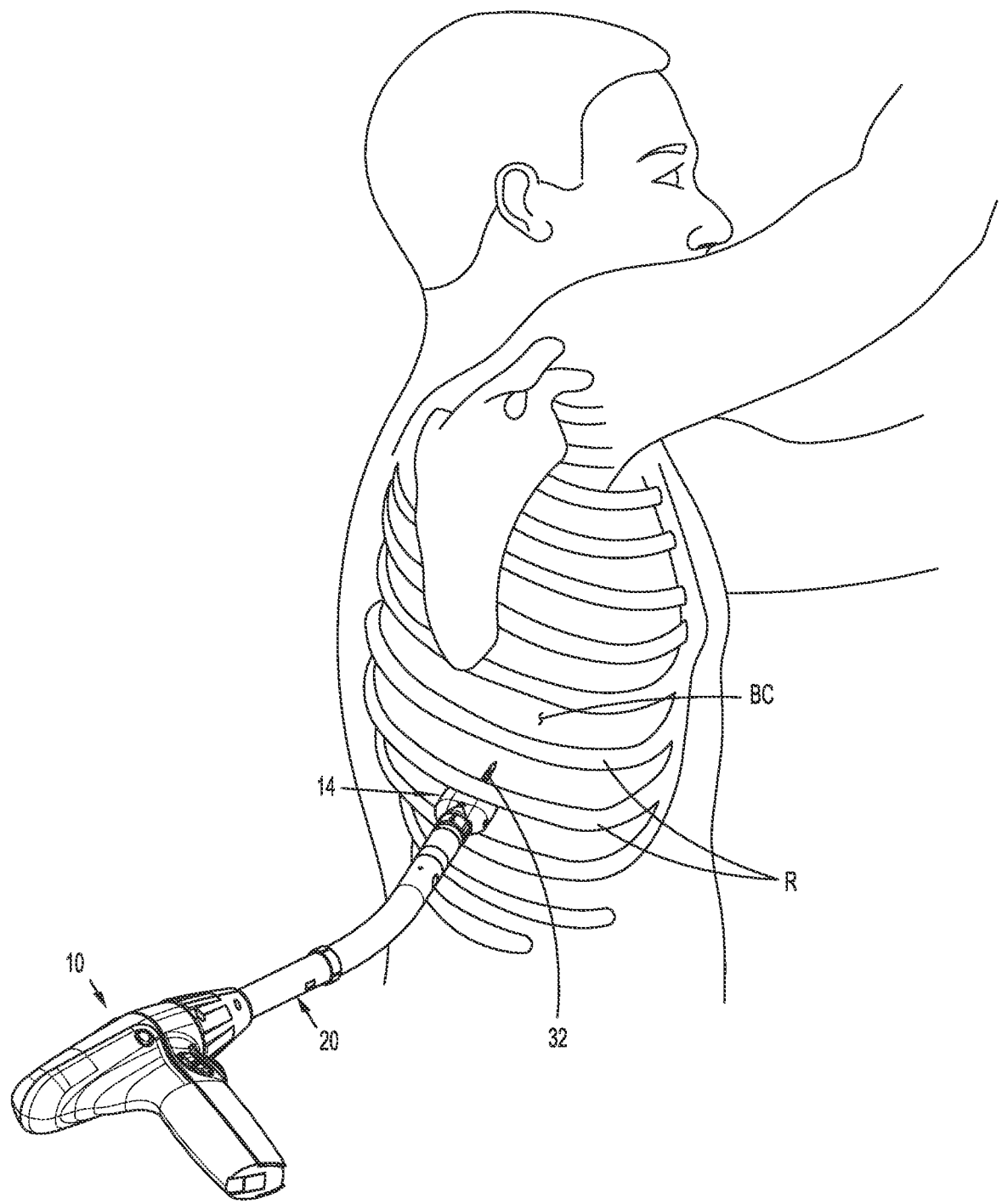
FIG. 14 is a side perspective view of the surgical stapling device shown in FIG. 1 as the reload assembly of the surgical stapling device is inserted through the intercostal space into a body cavity.

FIG. 14 illustrates the reload assembly 14 of the stapling device 10 as the reload assembly 14 is inserted through an intercostal space between ribs "R" of a patient "P" into the body cavity "BC" of the patient "P". Typically, a spreader (not shown) is used to spread adjacent ribs to accommodate passage of the reload assembly 14. The oval shape of the reload assembly 14 including the staple cartridge 120 allows the reload assembly 14 to be inserted through a smaller space to minimize any likelihood of rib fracture during spreading of the ribs.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   an elongate body having a distal portion and a proximal portion;
   an anvil retainer supported within and extending from the distal portion of the elongate body, the anvil retainer movable between an advanced position and a retracted position;
   a reload assembly supported on the distal portion of the elongate body, the reload assembly including a shell housing, a staple cartridge supported on the shell housing, staples supported within the staple cartridge, and a staple pushing member movable within the shell housing from a retracted position to an advanced position to eject the staples from the staple cartridge, the staple cartridge having an oval configuration with spaced side walls defining a width "W" and spaced end walls defining a length "L", wherein the length "L" is greater than the width "W"; and
   an anvil assembly supported on the anvil retainer and including an anvil, the anvil having an oval configuration that corresponds to the oval configuration of the staple cartridge, the anvil assembly movable in relation to the staple cartridge in response to movement of the anvil retainer between its retracted and advanced positions between open and clamped positions, wherein the anvil is in juxtaposed alignment with the staple cartridge in the clamped position.

2. The surgical stapling device of claim 1, wherein the anvil assembly includes the anvil, a center rod and an anvil head assembly, the anvil head assembly coupled to the center rod by a pivot member and movable in relation to the center rod between a tilted position and an operative position.

3. The surgical stapling device of claim 2, wherein the anvil head assembly defines a longitudinal axis and the center rod defines a longitudinal axis, the longitudinal axis of the anvil head assembly being aligned with the longitudinal axis of the center rod when the anvil head assembly is in the tilted position.

4. The surgical stapling device of claim 2, wherein the anvil head assembly is urged towards the tilted position.

5. The surgical device of claim 2, wherein the reload assembly includes a knife carrier and a knife that is supported on the knife carrier, the knife having an oval configuration and movable within the shell housing between retracted and advanced positions into engagement with the anvil head assembly.

6. The surgical stapling device of claim 5, wherein the anvil head assembly includes a housing having a post, a backup member, and a cut ring that is supported on the backup member, the post and the anvil defining an annular recess, the backup member and the cut ring movable within the annular recess from a retracted position to an advanced position.

7. The surgical stapling device of claim 5, wherein the backup member includes at least one finger that is engaged with the center rod when the backup member and the cut ring are in their retracted position, engagement between the at least one finger of the backup member and the center rod retaining the anvil head assembly in the operative position.

8. The surgical stapling device of claim 1, wherein the reload assembly includes a coupling mechanism, the coupling mechanism releasably coupling the reload assembly to the distal portion of the elongate body.

9. The surgical stapling device of claim 1, further including a handle assembly coupled to the proximal portion of the elongate body.

10. The surgical stapling device of claim 1, wherein the width "W" is about half of the length "L".

11. A reload assembly comprising:
   a shell housing, a staple cartridge supported on the shell housing, staples supported within the staple cartridge, and a staple pushing member movable within the shell housing from a retracted position to an advanced position to eject the staples from the staple cartridge, the staple cartridge having an oval configuration with spaced side walls defining a width "W" and spaced end walls defining a length "L", wherein the length "L" is greater than the width "W".

12. The reload assembly of claim 11, wherein the reload assembly includes a knife carrier and a knife that is supported on the knife carrier, the knife having an oval configuration and movable within the shell housing between retracted and advanced positions.

13. The reload assembly of claim 11, wherein the reload assembly includes a coupling mechanism, the coupling mechanism adapted to releasably couple the reload assembly to a body of a surgical stapling device.

14. The reload assembly of claim 11, wherein the width "W" is about half of the length "L".

15. The reload assembly of claim 11, wherein the spaced side walls are linear and the spaced end walls are curved.

16. An anvil assembly comprising:
a center rod; and
an anvil head assembly supported on the center rod by a pivot member and pivotable in relation to the center rod from an operative position to a tilted position, the anvil head assembly including a housing having a post, an anvil supported on the housing, a backup member, and a cut ring that is supported on the backup member, the post and the anvil defining an annular recess, the backup member and the cut ring movable within the annular recess from a retracted position to an advanced position, wherein the anvil has an oval configuration having a width "W" and a length "L", the length "L" being greater than the width "W".

17. The anvil assembly of claim 16, wherein the pivot member couples the center rod to the post of the anvil head assembly.

18. The anvil assembly of claim 16, wherein the width "W" is about half of the length "L".

19. The anvil assembly of claim 16, wherein the center rod includes a biasing member that urges the anvil head assembly towards the tilted position.

20. The anvil assembly of claim 16, wherein the anvil head assembly defines a longitudinal axis and the center rod defines a longitudinal axis, the longitudinal axis of the anvil head assembly being aligned with the longitudinal axis of the center rod when the anvil head assembly is in the tilted position.

* * * * *